(12) United States Patent
Lewkowicz et al.

(10) Patent No.: US 8,444,554 B2
(45) Date of Patent: *May 21, 2013

(54) FLOATABLE IN VIVO SENSING DEVICE AND METHOD FOR USE

(75) Inventors: Shlomo Lewkowicz, Tivon (IL); Daniel Gat, Haifa (IL); Arkady Glukhovsky, Nesher (IL); Semion Khait, Tiberias (IL); Gavriel Joseph Iddan, Haifa (IL); Harold Jacob, Jerusalem (IL); Christopher Paul Swain, London (GB)

(73) Assignee: Given Imaging Ltd., Yoqneam (IL)

( * ) Notice: Subject to any disclaimer, the term of this patent is extended or adjusted under 35 U.S.C. 154(b) by 1869 days.

This patent is subject to a terminal disclaimer.

(21) Appl. No.: 11/637,065

(22) Filed: Dec. 12, 2006

(65) Prior Publication Data

US 2007/0100208 A1 May 3, 2007

Related U.S. Application Data

(63) Continuation of application No. 10/150,492, filed on May 20, 2002, now Pat. No. 7,192,397.

(60) Provisional application No. 60/297,761, filed on Jun. 14, 2001.

(30) Foreign Application Priority Data

May 20, 2001 (IL) .......................... 143259

(51) Int. Cl.
*A61B 1/06* (2006.01)
*A61B 5/00* (2006.01)

(52) U.S. Cl.
USPC ............ 600/160; 600/309; 600/361; 600/549

(58) Field of Classification Search
USPC ................. 600/300, 301, 302, 309, 310, 322, 600/345, 361, 481, 505, 549, 109, 160–182
See application file for complete search history.

(56) References Cited

U.S. PATENT DOCUMENTS

| 3,144,017 A | 8/1964 | Muth |
| 3,683,389 A | 8/1972 | Hollis |

(Continued)

FOREIGN PATENT DOCUMENTS

| DE | 344 0177 | 5/1986 |
| IL | 143259 | 5/2001 |

(Continued)

OTHER PUBLICATIONS

Iddan, G. et al., "Wireless Capsule Endoscopy: the discomfort of internal gastrointestinal examination may soon be a thing of the past", Nature, vol. 405, No. 6785, p. 417, May 1, 2000.

(Continued)

*Primary Examiner* — Eric Winakur
(74) *Attorney, Agent, or Firm* — Pearl Cohen Zedek Latzer, LLP

(57) ABSTRACT

The invention relates to an in vivo sensing device having a specific gravity of about 1 or a volume to weight ratio that enables it essentially to float. In one embodiment the in vivo sensing device consists of an image sensor system and a buoyant body. The buoyant body, which is attached to the sensor system or which can optionally house one or more elements of the sensor system, keeps the sensor system essentially floating in a body lumen liquid.

7 Claims, 2 Drawing Sheets

U.S. PATENT DOCUMENTS

| | | | |
|---|---|---|---|
| 3,683,890 | A | 8/1972 | Beal |
| 3,971,362 | A | 7/1976 | Pope et al. |
| 4,178,735 | A | 12/1979 | Jackson |
| 4,262,632 | A | 4/1981 | Hanton et al. |
| 4,278,077 | A | 7/1981 | Mizumoto |
| 4,560,286 | A | 12/1985 | Wickersheim |
| 4,689,621 | A | 8/1987 | Kleinberg |
| 4,741,327 | A | 5/1988 | Yabe |
| 4,844,076 | A | 7/1989 | Lesho et al. |
| 4,940,997 | A | 7/1990 | Hamlin et al. |
| 5,279,607 | A | 1/1994 | Schentag et al. |
| 5,437,274 | A | 8/1995 | Khoobehi et al. |
| 5,549,109 | A | 8/1996 | Samson et al. |
| 5,604,531 | A | 2/1997 | Iddan et al. |
| 5,819,736 | A | 10/1998 | Avny et al. |
| 5,833,603 | A | 11/1998 | Kovacs et al. |
| 5,984,875 | A | 11/1999 | Brune |
| 5,993,378 | A | 11/1999 | Lemelson |
| 6,099,482 | A | 8/2000 | Brune et al. |
| 6,149,581 | A | 11/2000 | Klingenstein |
| 6,228,048 | B1 | 5/2001 | Robbins |
| 6,240,312 | B1 | 5/2001 | Alfano et al. |
| 6,324,418 | B1 | 11/2001 | Crowley et al. |
| 6,547,723 | B1 | 4/2003 | Ouchi |
| 6,632,175 | B1 | 10/2003 | Marshall |
| 7,009,634 | B2 | 3/2006 | Iddan et al. |
| 2001/0017649 | A1 | 8/2001 | Yaron |
| 2001/0025135 | A1 | 9/2001 | Naito et al. |
| 2001/0035902 | A1 | 11/2001 | Iddan et al. |
| 2001/0051766 | A1 | 12/2001 | Gazdzinski |
| 2002/0103417 | A1 | 8/2002 | Gazdzinski |
| 2002/0198439 | A1 | 12/2002 | Mizuno |
| 2003/0045790 | A1 | 3/2003 | Lewkowicz et al. |
| 2003/0171648 | A1 | 9/2003 | Yokoi et al. |
| 2003/0171649 | A1 | 9/2003 | Yokoi et al. |
| 2003/0171652 | A1 | 9/2003 | Yokoi et al. |
| 2003/0195415 | A1 | 10/2003 | Iddan |
| 2003/0214579 | A1 | 11/2003 | Iddan |
| 2003/0214580 | A1 | 11/2003 | Iddan |
| 2003/0216622 | A1 | 11/2003 | Meron et al. |
| 2004/0027459 | A1 | 2/2004 | Segawa et al. |

FOREIGN PATENT DOCUMENTS

| | | |
|---|---|---|
| JP | 57-45833 | 3/1982 |
| JP | 3-289779 | 12/1991 |
| JP | 4-109927 | 4/1992 |
| JP | 1992-144533 | 5/1992 |
| JP | 4144533 | 5/1992 |
| JP | 4-180736 | 6/1992 |
| JP | 5015515 | 1/1993 |
| JP | 7116262 | 5/1995 |
| JP | H7-111985 | 5/1995 |
| JP | 7289504 | 11/1995 |
| JP | H7-289504 | 11/1995 |
| JP | H8-503384 | 4/1996 |
| JP | H11-101796 | 4/1999 |
| JP | H11-201889 | 7/1999 |
| JP | 2000342527 | 12/2000 |
| JP | 2001-112740 | 4/2001 |
| JP | 2001-137182 | 5/2001 |
| JP | 2001-224551 | 8/2001 |
| JP | 2001-224553 | 8/2001 |
| JP | 4674038 | 1/2011 |
| WO | WO 92/21307 | 12/1992 |
| WO | WO 98/11816 | 3/1998 |
| WO | WO 00/22975 | 4/2000 |
| WO | WO 00/33738 | 6/2000 |
| WO | WO 00/54701 | 9/2000 |
| WO | WO 01/08548 | 2/2001 |
| WO | WO 01/10291 | 2/2001 |
| WO | WO 01/50941 | 7/2001 |
| WO | WO 01/65995 | 9/2001 |
| WO | WO 02/067593 | 8/2002 |
| WO | WO 02/094337 | 11/2002 |
| WO | WO 2004/028336 | 4/2004 |

OTHER PUBLICATIONS

Supplementary European Search Report for European Application No. EP 02 73 3169, dated Oct. 29, 2008.
U.S. Appl. No. 10/166,025, filed Jun. 11, 2002, Lewkowics et al.
U.S. Appl. No. 10/213,345, filed Aug. 7, 2002, Glukhovsky et al.
The Radio Pill, Rowlands et al., British Communications and Electronics, Aug. 1960, pp. 598-601.
Wellesley company sends body monitors into space—Crum, Apr. 1998.
Wireless transmission of a color television moving image from the stomach using a miniature CCD camera, light source and microwave transmitter, Swain CP, Gong F, Mills TN, Gastrointest Endosc 1997; 45:AB40.
BBC News Online—Pill camera to 'broadcast from the gut', Feb. 21, 2000, www.news.bbc.co.uk.
Wang et al., "Integrated Micro-Instrumentation for Dynamic Monitoring of the Gastro-Intestinal Tract", Presented at IEEE Instrumentation and Measurement Technology Conference, May 2002, Anchorage, AK, USA, www.see.ed.ac.uk/Naa.publications.html.
Robots for the future—Shin-ichi et al., Nov. 29, 2001.
Video Camera to "TAKE"—RF System lab, Dec. 25, 2001.
www.rfnokia.com—NORIKA3, Dec. 24, 2001.
International Search Report of Application No. PCT/IL02/00392 Dated Dec. 16, 2002.
English Translation of Office Action for Japanese Patent Application No. 2009-235357 dated Oct. 26, 2010.
Office Action for Japanese Patent Application No. 2009-235357 dated Jun. 21, 2011.

FLOATABLE IN VIVO SENSING DEVICE AND METHOD FOR USE

CROSS REFERENCE TO RELATED APPLICATIONS

This application is a Continuation Application of U.S. patent application Ser. No. 10/150,492, filed May 20, 2002, now U.S. Pat. No. 7,192,397 entitled "Floatable In Vivo Sensing Device and Method for Use", which in turn claims priority from both U.S. Provisional Application No. 60/297,761, filed Jun. 14, 2001, entitled "A Floatable In Vivo Sensing Device", and from Israeli Patent Application No. 143259, filed May 20, 2001, entitled "A Method of Moving an Object through the Colon", all of which are incorporated in their entirety herein by reference.

FIELD OF THE INVENTION

The present invention relates to the field of in vivo sensing. Specifically, the present invention relates to a floatable in vivo sensing device that can be carried by liquid.

BACKGROUND OF THE INVENTION

In vivo sensors are non invasive tools used in diagnosis of diverse body systems. For example, ingestible devices may be used for sensing in vivo conditions in the gastrointestinal (GI) tract, such as, temperature, pH or pressure. Ingestible imaging devices can be used for imaging the gastrointestinal tract. For example, a capsule comprising a sensor, such as an image sensor, may be ingested and moved passively through the small intestine by peristalsis while imaging or otherwise sensing the small intestine. However, passive movement of objects through larger body lumens, such as the large intestine, may be slower and unpredictable. The large intestine, or colon, whose main function is to remove much of the water from the stool and to store the stool, begins with the cecum, a small saclike evagination, then continues with the ascending colon, from the appendix in right groin up to a flexure at the liver, transverse colon, liver to spleen, descending colon, spleen to left groin, then sigmoid (S-shaped) colon back to midline and anus. The colon has three longitudinal muscle bands whose actions assist movement through the colon.

It is sometimes advantageous to move objects through the colon independently of the natural action of the colon muscles. For example, delivery of a medicament to a specific location in the colon may be time dependant and cannot rely on the natural movement in the colon. Also a device for imaging the colon might benefit from being actively moved through the colon so as to efficiently view the colon.

Current methods of moving objects, especially imaging devices, through the colon involve the use of endoscopes, typically colonoscopes, which are expensive and inconvenient for patient use, and do not always enable to reach distal parts of the colon, such as the cecum and the right colon.

SUMMARY OF THE INVENTION

An embodiment of the present invention provides an essentially floatable sensing device that can be carried by liquid. The sensing device according to an embodiment of the invention is useful in sensing, such as by imaging, lumens containing or capable of containing a bulk of liquid. One example of such a lumen is the large intestine. The essentially floatable sensing device of the invention is carried by the liquid and can thus be moved through the lumen together with the bulk of liquid.

According to one embodiment of the invention the in vivo sensing device has a specific gravity (SG) of about 1.0 or a volume to weight ratio that enables it essentially to float.

In one embodiment the in vivo sensing g device comprises a sensor system and a buoyant body. The buoyant body, which can optionally house one or more elements of the sensor system, may have a specific gravity of about 1.0, which is just about floating, or a volume to weight ratio that enables it essentially to float in a body lumen liquid. In another embodiment of the invention the buoyant body is a buoy attached to a sensor system, which keeps the sensor system essentially floating in a body lumen liquid.

The sensor system may comprise any sensor suitable for sensing in vivo environment parameters, such as pH, temperature, conductivity, shear, pressure and so on. The sensor system can include all the elements necessary for in vivo sensing, as known in the art. In one embodiment the sensor is an image sensor.

According to a further embodiment of the invention there is provided a method for sensing body lumens, such as the stomach or large intestine. Typically, the method involves moving an in vivo sensor through the body lumen. The method, according to one embodiment of the invention, comprises the steps of providing an essentially buoyant sensor system and sensing the body lumen. Preferably the body lumen contains a bulk of liquid. In an embodiment of the invention the method is used for sensing a patient's large intestines and may comprise the steps of clearing the large intestine of its contents, for example by using standard laxatives and prep. solutions and filling the large intestine with a liquid.

According to yet another embodiment of the invention high osmotic pressure compositions, such as contrast agents, are utilized to assist in the movement of objects though the colon.

BRIEF DESCRIPTION OF THE DRAWINGS

The present invention will be understood and appreciated more fully from the following detailed description taken in conjunction with the drawings in which.

DETAILED DESCRIPTION OF THE INVENTION

Figure 1:
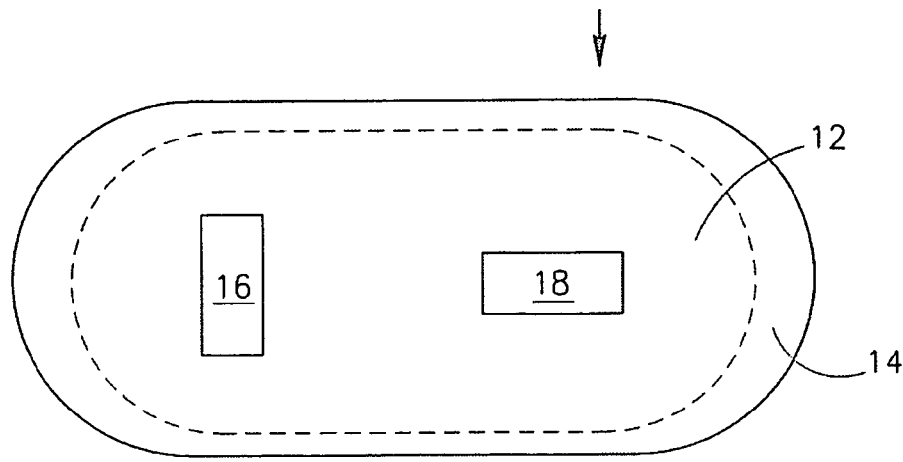
FIG. 1 is a schematic illustration of a floatable sensing device in accordance with an embodiment of the invention.

A sensing device, according to an embodiment of the invention, is schematically illustrated in FIG. 1. The sensing device 10 is an autonomous capsule shaped device and can thus be easily moved through the small intestine. However, it should be appreciated that an autonomous sensing device according to different embodiments of the invention can have any shape or design suitable for being inserted and moved through body lumens, such as the gastrointestinal tract, the reproductive system, blood vessels, etc.

Device 10 includes a sensor system 12 and a buoyant body 14. In one embodiment, the buoyant boy 14 is essentially a part of the sensor system 12. The sensor system 12 may be a pH sensing system as known in the art, an image sensor as known in the art or other known in vivo sensing systems such as an in vivo temperature measuring system, a pressure sensor, a shear sensor, a sensor of electrical conductivity and other known in vivo sensors. In other embodiments a combination of sensors may be used. In one embodiment of the invention the sensor system 12 may be an imaging device comprising, for example, at least one image sensor (such as image sensor 16), one or more illumination source (not shown) and one or more transmitter for transmitting image signals to an external receiving system (not shown). In vivo imaging systems that can be utilized with the present invention are described, for example, with reference to FIG. 2A below, or in WO 01/65995 or in U.S. Pat. No. 5,604,531. In another embodiment the sensor system 12 includes a temperature measuring system. A temperature measuring system according to an embodiment of the invention may comprise an image sensor 16 having an image sensing module in communication with an integrating unit (not shown) for detecting the dark current of the image sensor image sensing module and for calculating the temperature of the image sensor. The integrating unit further calculates the temperature of the environment or the temperature of the environment may be calculated, based on data from the integrating unit, by a separate unit that is in communication with the integrating unit. A temperature measuring system that may be utilized according to an embodiment of the invention is described, for example, in WO 01/10291.

Typically, the sensor system 12 is powered by a battery 18, however other embodiments are possible, for example, the sensor system may be power induced by an external electromagnetic field.

The buoyant body 14 lends a volume to weight ratio, or a specific gravity to the device 10 that enables it to float in a liquid filled lumen.

SG—specific gravity—is weight [gr.]/weight of water in the amount displaced by the device 10 (when reaching maximal volume) or for sealed objects, SG is weight [gr]/volume [cubic cm]. Typically, buoyant body 14 can be filled with a substance lighter than the body lumen liquid, such as gaseous $CO_2$, $O_2$ or air.

Figure 2A:
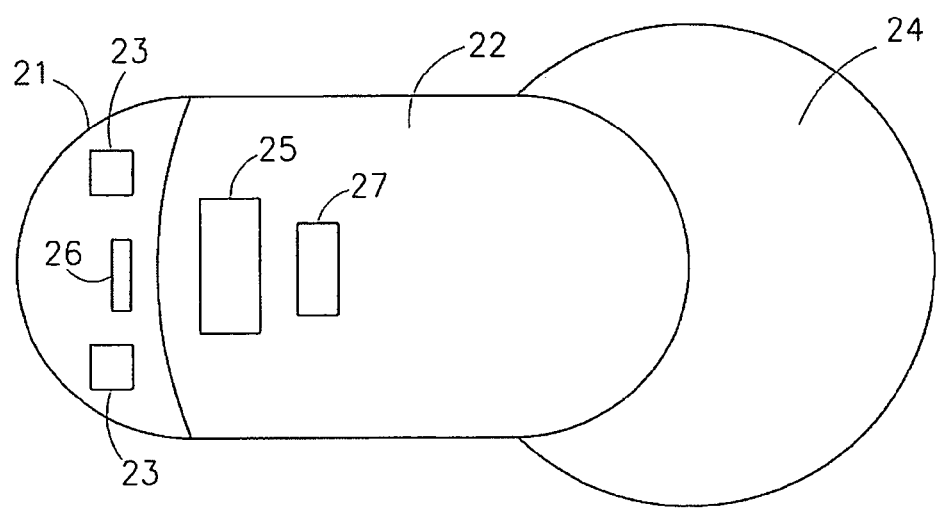
FIG. 2A is a schematic illustration of a floatable sensing device in accordance with another embodiment of the invention.

In another embodiment of the invention schematically illustrated in FIG. 2A, the sensor system is an image sensor system 22 and the buoyant body is an inflatable buoy 24. The buoy 24 may be packaged such that it is not buoyant while in packaging. However, release of the buoy from its packaging lends buoyancy to the sensor system. The buoy may be released from its packaging at a desired location or point in time, such that the sensor system 22 may acquire buoyancy according to specific requirements. For example, the floatable sensing device according to an embodiment of the invention may be ingested and moved by peristalsis through the small intestine while its buoy is packaged. When the device enters the large intestine the buoy is released from its packaging and the device can then float in the bulk of liquid in the large intestine and be carried by the bulk of liquid to all areas of the large intestine. Thus, the device is moved through the large intestine, effectively sensing the lumen. The mechanisms by which the buoy is released from its packaging can be externally controlled or automatically controlled as will be further described below.

The image sensor system 22 includes an image sensor 26, for example a charge coupled device (CCD) or a complementary metal oxide semiconductor (CMOS) image sensor, illumination sources 23, an optical system which includes an optical window 21 through which the body lumen is illuminated and imaged and lenses and/or mirrors (not shown) for collimating light, a transmitter 25 for transmitting image signals to an external receiving system (not shown) and a battery 27 for supplying power to the elements of the image sensor system 22.

The inflatable buoy 24 is a typically elastic compartment containing air, which is attached to the image sensor system 22. The inflatable buoy 24 will lend buoyancy to the image sensor system 22 such that it can essentially float in the liquid filling a body lumen and be thus moved through the body lumen, obtaining images of essentially all parts of the body lumen.

Figure 2B:
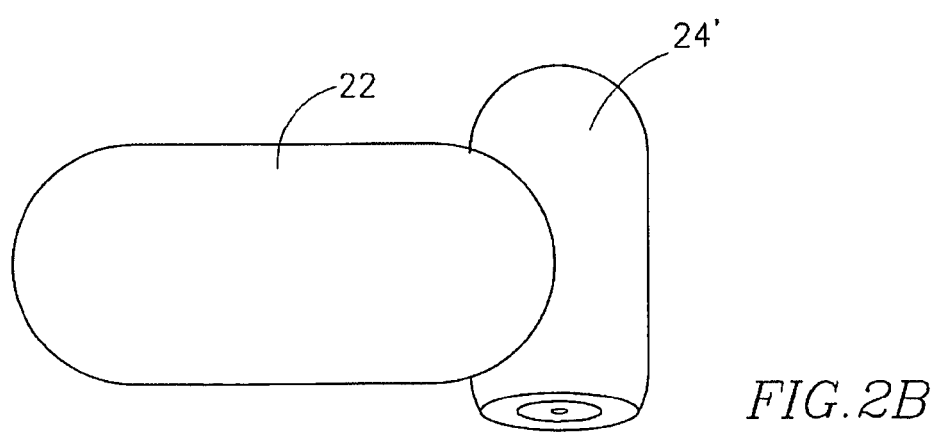
FIG. 2B is a schematic illustration of a floatable sensing device with a packaged buoy in accordance with an embodiment of the invention.

In another embodiment of the invention, schematically illustrated in FIG. 2B an image sensor system 22, as above, comprises an inflatable buoy 24'. The inflatable buoy 24' is rolled and packaged to a small size. In its packaged form inflatable buoy 24' typically does not lend buoyancy to the image sensor system 22. The inflatable buoy 24' may be released from its packaging by a manually or automatically controlled mechanism, at a desired location in vivo. For example, the inflatable buoy 24' may contain gas releasing granules such as crystalline sodium bicarbonate, E-Z GasII effervescent granules by EZEM of NY, USA or similar oxygen releasing granules. Typically, these granules release gas (such as $CO_2$ or oxygen) upon contacting liquid. In an embodiment of the invention inflatable buoy 24' contains two compartments (not shown), one compartment containing gas releasing granules (for example 100 mg of granules) and the other containing a drop of liquid (for example 0.1 cc of water or saline). The compartments are kept separate while the inflatable buoy 24' is in its packaged form. Once the packaging is opened, the two compartments are merged and the drop of liquid contacts the gas releasing granules. Gas is released into the now unpacked buoy inflating the buoy and enhancing buoyancy.

The packaging can be achieved by a manually controlled mechanism, such as a bimorph material mechanism that could change configuration in accordance with controllable conditions, such as a temperature or electric voltage gradient, as known in the art. Alternatively, the packaging mechanism can be time dependent or dependant on in vivo conditions such as pH or enzymatic activity. For example, packaging can be effected by a hydrocarbon such as a gelatin capsule which encases the image sensor system 22 and the inflatable buoy 24' and keeps the inflatable buoy 24' in a packaged form. According to one embodiment, the gelatin capsule slowly dissolves in the liquid present in the stomach, thereby releasing the inflatable buoy. The gelatin capsule, such as gelatin capsules provided by Capsugel USA, can be made to dissolve at a specific location along the GI tract, as known in the field of sustained release mechanisms. Thus, a device comprising image sensor system 22 and inflatable buoy 24' can be encased in a hydrocarbon capsule while moving through certain parts of a patient's GI tract and free of the encapsulation in other parts of the GI tract. While free of the encapsulation, inflatable buoy 24' will be inflated and the device will be able to essentially float in the GI tract liquid. In another embodiment the packaging can be effected by degradable sutures known in the art, such that the packaging of the inflatable buoy 24' is released when the suture is degraded.

Figure 3A:
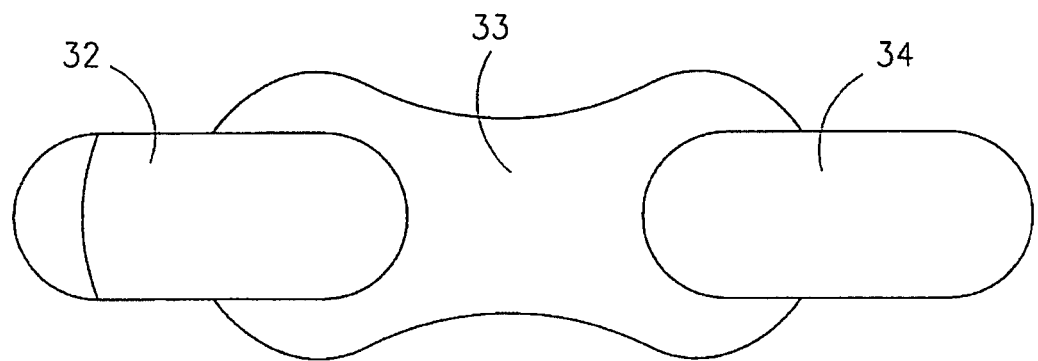
FIGS. 3A and 3B are schematic illustrations of a floatable sensing device in accordance with yet other embodiments of the invention.
Figure 3B:
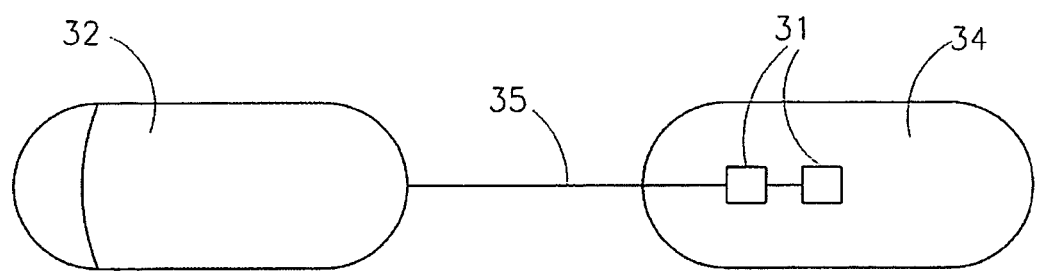

Another embodiment of the invention is schematically illustrated in FIGS. 3A and 3B, in which a sensor system 32, such as an imaging sensor system or other sensing systems, for example, those described above, is attached to a buoy 34, which is typically a light vessel made of, for example, plastic such as isoplast, filled with a substance lighter than the body lumen liquid. In certain embodiments of the invention the buoy 34 can contain accessory components or materials, such as additional batteries 31.

The sensor system 32 and the buoy 34 can be attached by a flexible sleeve 33 (FIG. 3A), which, if filled with a substance lighter than the body lumen liquid, can also assist in enhancing the buoyancy of the sensor system 32. Alternatively, the sensor system 32 and the buoy 34 can be attached by a wire 35 (FIG. 3B). The wire 35 can couple sensor system 32 and the buoy 34, for example, if electrical coupling is needed for utilizing the additional batteries 31 by the sensor system 32.

According to a further embodiment of the present invention there is provided a method for sensing body lumens, such as the stomach or large intestine. In an embodiment of the invention a floatable sensing device, such as the devices described above, is inserted in vivo. The sensing device may include a sensor system and a buoyant body. The buoyant body may be inflated prior to being inserted in vivo or may be inflated at a specific location or point in time while in a patient's body, as described above. Preferably, the sensor system and buoyant body are placed in a body lumen containing a bulk of liquid. More preferably there is a flow of liquids through the body lumen, upon which the sensor system is carried through the body lumen. Thus, this method can be used, in one embodiment, for imaging or otherwise sensing a patient's large intestines. In one embodiment the patient's large intestine is initially cleared of its contents, for example by inducing bowel movement by administering a laxative or an enema. Further, the patient's large intestine is filled with a liquid, for example by drinking high osmolarity liquids, which retain liquids within the large intestine for longer periods. Typically, a liquid loaded intestine and/or additional laxatives, administered while the sensor system is in the large intestine, will induce bowel movement and cause a flow of the bulk of liquids in the large intestine. The induced flow will enhance movement of the sensor system through the large intestine, thereby facilitating sensing of most areas of the lumen.

According to one embodiment of the invention an imaging device for imaging the GI tract can be moved through the large intestine by utilizing, for example, a high osmotic pressure composition that is essentially not absorbed by the intestine. According to other embodiments an object other than an imaging device, for example a device for sustained release of medicaments to the colon, can be moved through die large intestine by utilizing a high osmotic pressure composition that is essentially not absorbed by the intestine. Objects moved through the large intestine utilizing a high osmotic pressure composition according to an embodiment of the invention may or may not be floatable.

A wireless in vivo imaging device such as the sensor systems described above or a device including a compartment for collecting or distributing substances from or to the GI tract, such as the device described in WO00/22975, can be moved through the large intestine according to an embodiment of the invention such that it can be used for diagnostic and/or for therapeutic purposes.

In one embodiment, an in vivo imaging device is introduced into the GI tract by utilizing a colonoscope. In another embodiment the in vivo imaging device is ingested by a patient and traverses the small intestine pushed along by natural peristalsis. When the device reaches the cecum it may remain in the cecum for typically long periods of time. According to an embodiment of the invention a high osmotic pressure composition that is essentially not absorbed by the intestine, such as a contrast agent, may be administered to the patient. The high osmotic pressure composition typically progresses through the small intestine arriving at the cecum. The composition usually progresses in the intestine faster than the device, pushing in its progression the device through the different parts of the colon. An example of a high osmotic pressure composition that may be used according to an embodiment of the invention is barium sulfate or gastrografin. The osmotic pressure of gastrografin at 37° C. is 55.1 Atm and its osmolality is 2.15 (osm/kg $H_2O$).

A wireless ingestible imaging capsule as described above was administered under Helsinki Committee guidelines to normal healthy volunteers in the standard fashion. The volunteers underwent standard colonoscopic preparation consisting of a 24-hour liquid diet and 4 ounces of Fleet phosphasoda the evening before and the morning of the procedure. The volunteers were encouraged to drink a large volume of fluid before and after ingestion of the capsule. The passage of the capsule was monitored on-line. The volunteers were given 8 ounces of gastrografin diluted as for regular body CT examination [5%], every 15 minutes starting 2.5 hours after ingestion of the capsule, up to a total of 2 liters. The volunteers were allowed to eat a normal meal 4 hours after ingestion of the capsule.

Results: In one case, the gastric emptying time was 42 minutes, and the capsule reached the cecum after 4 hours and 16 minutes. The capsule was excreted from the colon 22 hours after ingestion. Images of various parts of the colon were acquired for more than 3 hours. In the second case, gastric emptying occurred after 8 minutes, and the capsule reached the cecum after 8 hours. Images of all parts of the colon were acquired for 2.5 hours. The capsule was excreted after 10.5 hours, still working.

Conclusion: The first successful passage through the right colon in the first case and the entire colon in the second case of a functioning imaging capsule using a novel technique is described. The use of gastrografin was based on clinical observation in GI radiological procedures, such as CT. This agent may have an important role in the movement of the imaging capsule through the colon.

Gastrografin contains a mixture of sodium amidotrizoate and meglumine amidotrizoate in a proportion of 10:66 (amidotrizoic acid or diatrizoic acid: 3,5-bis-acetamido-2,4,6-triiodobenzoic acid). 1 mL gastrografin contains sodium amidotrizoate 100,00 mg and meglumine amidotrizoate 660,00 mg (sodium diatrizoate and meglumine diatrizoate) in aqueous solution plus flavorings and a wetting agent. The contrast-giving substances in gastrografin are salts of amidotrizoic acid in which the X-ray absorbing iodine is present in stable chemical bond. Following oral administration only about 3% of the amidotrizoic acid is absorbed by the stomach and intestines. This portion is eliminated mainly via the kidneys.

Gastrografin can be used either orally or as an enema. Gastrografin typically travels through the colon faster than the capsule and is a clear fluid, allowing a clear view of the colon. Another advantage of gastrografin is its opacity to x-ray, allowing direct view in fluoroscopy and enabling monitoring of the passage of the capsule through the GI tract.

It will be appreciated by persons skilled in the art that the present invention is not limited to what has been particularly shown and described hereinabove. Rather the scope of the present invention is defined only by the claims which follow:

The invention claimed is:

1. A device for obtaining image data from within a liquid containing body lumen, the device comprising:
   a housing configured to be ingested, the housing having an optical window through which the body lumen is illuminated and imaged, said housing enclosing therein an illumination source to illuminate the body lumen and an image sensor to image the body lumen, wherein the device has a specific gravity of about 1.

2. The device according to claim 1 comprising a transmitter to wirelessly transmit image data from the device.

3. The device according to claim 1 wherein the housing is capsule shaped.

4. The device according to claim 3 wherein the optical window is at an end of the housing.

5. The device according to claim 1 further comprising a sensor to sense an in vivo environment parameter.

6. The device according to claim 5 wherein the sensor is to sense a parameter selected from a group consisting of: pH, temperature, conductivity, shear and pressure.

7. The device according to claim 5 wherein the body lumen is a gastrointestinal tract.

* * * * *